(12) United States Patent
Uchikoshi

(10) Patent No.: US 6,436,258 B1
(45) Date of Patent: Aug. 20, 2002

(54) GALVANIC-CELL GAS SENSOR

(75) Inventor: Shoichi Uchikoshi, Tokyo (JP)

(73) Assignee: Riken Keikico., Ltd., Tokyo (JP)

( * ) Notice: Subject to any disclaimer, the term of this patent is extended or adjusted under 35 U.S.C. 154(b) by 0 days.

(21) Appl. No.: 09/693,911

(22) Filed: Oct. 23, 2000

(30) Foreign Application Priority Data

Aug. 11, 2000 (JP) ........................................ 2000-243593

(51) Int. Cl.⁷ ............................................. G01N 27/404
(52) U.S. Cl. ..................................... 204/415; 205/783
(58) Field of Search .......................... 204/415; 205/782, 205/782.5, 783

(56) References Cited

U.S. PATENT DOCUMENTS

| | | | | |
|---|---|---|---|---|
| 3,322,662 A | * | 5/1967 | Mackereth | |
| 3,406,109 A | * | 10/1968 | Molloy | |
| 3,429,796 A | * | 2/1969 | Lauer | |
| 3,510,421 A | * | 5/1970 | Gealt | |
| 3,948,746 A | * | 4/1976 | Poole | |
| 4,175,028 A | * | 11/1979 | Payton | |
| 5,395,507 A | * | 3/1995 | Aston et al. | |

* cited by examiner

Primary Examiner—T. Tung
(74) Attorney, Agent, or Firm—Connolly Bove Lodge & Hutz, LLP

(57) ABSTRACT

A galvanic-cell gas sensor includes casings containing a diaphragm permitting the permeation of gas to be detected but having a water-repelling property, a cathode provided on the back side of the diaphragm, an anode formed by electrolytically coating a layer of lead (Pb) on an electrically conductive material having a corrosion resistance to electrolyte so as to leave a portion thereof uncoated to serve as a lead, and a sheet impregnated with electrolyte before assembly and disposed between the cathode and anode, with the diaphragm positioned so as to be exposed to the atmosphere.

11 Claims, 3 Drawing Sheets

GALVANIC-CELL GAS SENSOR

FIELD OF THE INVENTION

This invention relates to a galvanic-cell gas sensor comprising a cathode and an anode adapted to come into contact with a gas to be detected and sealed in an electrolyte.

DESCRIPTION OF THE INVENTION

A conventional galvanic-cell gas sensor comprises a holder serving as a container to hold an acid electrolyte and having a window and a diaphragm of a water-repellent film of a macromolecular fluorochemical sealed therein, with a cathode of gold (Au) disposed in a segment holding the electrolyte and an anode of lead (Pb) disposed apart from the cathode.

This type of sensor holding an electrolyte has been required to have a liquid-tightness that in turn calls for a complex sealing structure. The use of lead as the unnecessarily large anode has made it extremely difficult to reduce the size of the container.

The anode A has a rod portion B at one end thereof formed by casting or other method or a rod B' of a metal having a high corrosion resistance to the electrolyte and planted on the anode, as shown in FIG. 5. Therefore, the anode has been disproportionally sized considering the service life of the sensor, and has hampered the size reduction of the sensor.

SUMMARY OF THE INVENTION

This galvanic-cell gas sensor eliminates the need to form the anode lead segment on the anode from lead (Pb) sheet, while permitting a reduction in the sensor size by coating an appropriate amount of Pb proportional to the sensor life on the anode through accurate control of coating time.

This galvanic-cell gas sensor eliminates the need to form the lead segment on the anode from lead sheet while permitting to reduce the sensor size by coating an appropriate amount of lead proportional to the sensor life on the anode through accurate control of coating time.

Thus, the object of this invention is to provide a galvanic-cell gas sensor of smaller size by making the anode size proportional to the sensor life.

DESCRIPTION OF THE PREFERRED EMBODIMENTS

Figure 1:
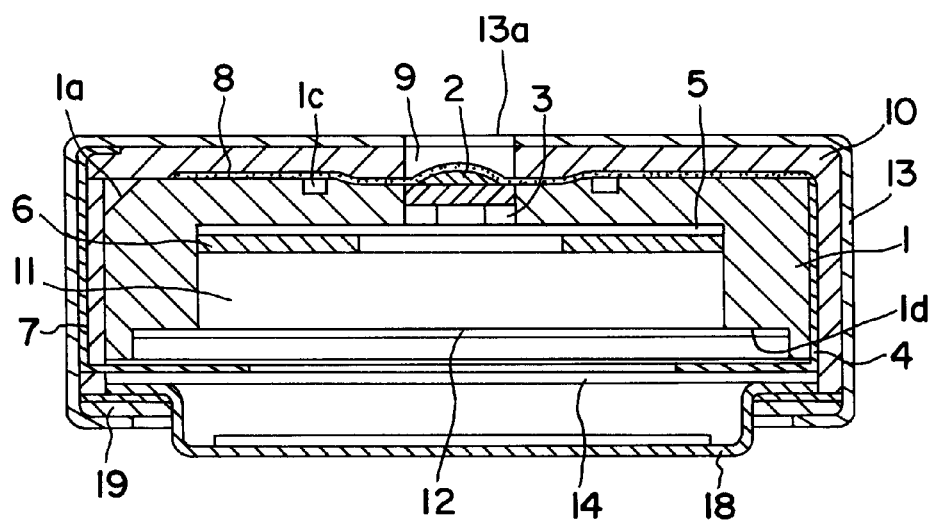
FIG. 1 is a cross-sectional view of an embodiment of a galvanic-cell gas sensor according to this invention.
Figure 2:
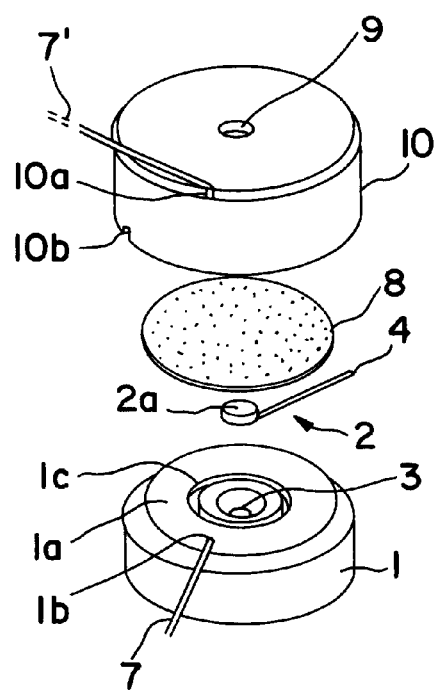
FIG. 2 is a perspective view of component elements, notably an electrode-holding frame, of the same gas sensor.

FIG. 1 shows a galvanic-cell gas sensor according to this invention. An electrode-holding frame 1 consisting of a closed-end cylinder has a through hole 3 at the center of the top thereof. The through hole 3 having a diameter substantially equal to the outside diameter of a cathode 2 is adapted to hold the cathode 2 therein with the top of the cathode 2 protruding somewhat above the top edge thereof, as shown in FIG. 2. A cathode 2 whose top surface 2a is convexly shaped is put in the upper part of the through hole 3 in the electrode-holding frame 1. A lead 4 is run from the cathode 2 to the bottom of the electrode-holding frame 1 over the top and peripheral surfaces thereof. The lead 4 is pulled out to run in the nonradial direction over the top surface 1a of the electrode-holding frame 1 and held in contact therewith over a relatively long distance.

A sheet 5 to hold an electrolyte and an anode 6 described later are laminated on the rear side of the electrode-holding frame 1. A lead 7 is pulled from anode 6 through a through hole 1b in the electrode-holding frame 1 so as to run somewhat off the radial direction as shown in FIG. 2.

To the top surface of the electrode-holding frame 1 is fastened a gas-permeable water-repellent film 8, such as a film of propylene fluoride copolymer, whose diameter is somewhat smaller than the diameter of the electrode-holding frame 1 and larger than that of the through hole 3 with an adhesive bond applied to the outer edge thereof. An annular groove 1c provided outside the through hole 3 takes in any excess adhesive bond so as to prevent the adhesive bond from flowing into the cathode 2.

A closed-end cap 10 having a center through hole 9 of electrically insulating material, such as rubber, is placed over the water-repellent film 8. The rear surface of the cap 10 is concaved with respect to the top surface of the electrode-holding frame 1, while the cathode 2 having a substantially convex surface is placed so as to lie substantially flush with the top surface 1a. As such, the water-repellent film 8 becomes spherically curved when pressed under the cap 10.

In this state, the lead 7 of the anode 6 pulled out through the through hole 1b in the top surface 1a of the electrode-holding frame 1 and a through hole 10a in the top corner of the cap 10 is run over the top surface of the cap 10 to a point opposite the lead 4 of the cathode 2 (as designated by reference numeral 7' with a dot-dash line in FIG. 2). Then, the lead 7 is bent so as to run along the peripheral surface of the cap 10 and taken in through a notch 10b. The lead 7 thus detoured establishes a definite conductive relationship with the metal cap proper 13 by increasing the area of contact therewith to a maximum.

A sealing film 12 of macromolecular substance, such as a film of tetrafluoroethylene copolymer, fit against a stepped part 1d formed in the opening of the electrode-holding frame and held by the metal cap proper 13 having a window 13a facing the cathode 2 defines a space to hold the electrolyte outside of which a circuit board 14 is provided.

Figure 3:
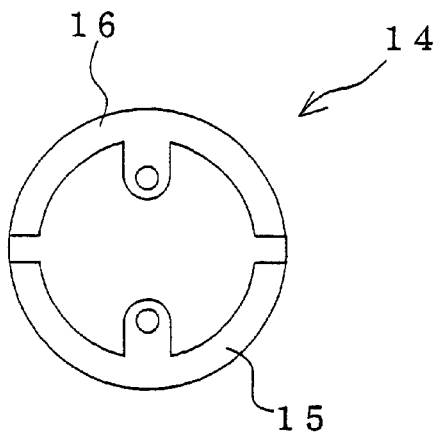
FIGS. 3(a) and 3(b) show the top and bottom conducting patterns of a circuit board mounted in the same gas sensor.
Figure 3:
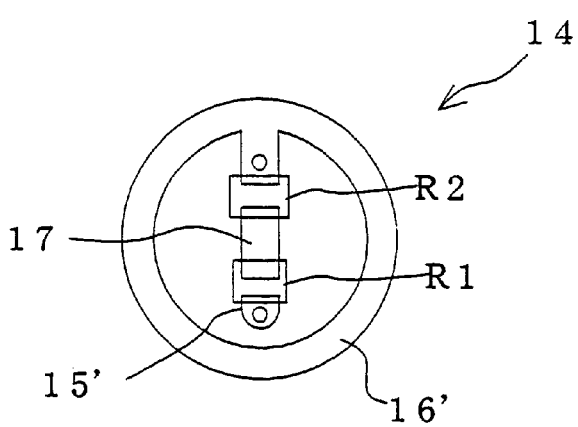

The circuit board 14 has conducting patterns 15 and 16 on the surface thereof facing the anode 6 that are adapted to be connected to the leads 4 and 7 of the cathode 2 and anode 6 as shown in FIG. 3(a). The reverse side of the circuit board 14 has an annular conductive pattern 16' to connect to the anode 6 along the periphery thereof and a terminal conductive pattern 15' to connect to the cathode 2 in the center thereof. A relay terminal 17, to which a temperature-compensating thermal sensing resistor R1 and an output standardizing relay R2 are connected, is provided between the conductive patterns 15' and 16'.

A metal bottom cap 18 is fit in the cap 10 whose inside diameter is substantially equal to the outer periphery of the metal bottom cap 18. An annular electrically insulating plate 19 is provided around the metal bottom cap 18 to caulk the opening in the metal cap 13.

Thus, the anode 6 establishes a conductive relationship with the metal cap proper 13 by means of the lead 7 that comes into contact with the bottom and inner wall and the bottom of the top surface of the metal cap proper 13, while the cathode 2 establishes a conductive relationship by means of the metal bottom cap 18 that resiliently comes into contact with the annular conductive pattern 16' on the circuit board 14. Therefore, the sensor output can be taken out from the side and bottom of the cap, as with a button cell.

Figure 4:
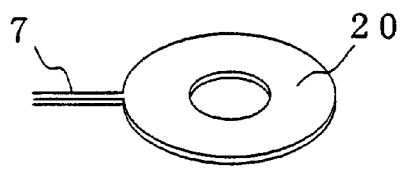
FIGS. 4(a) and 4(b) are cross-sectional views of a substrate making up the anode and an embodiment of the anode.
Figure 4:
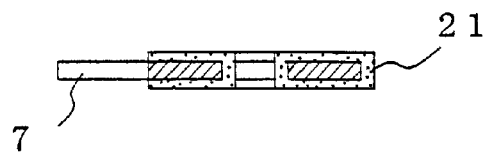
Figure 5:
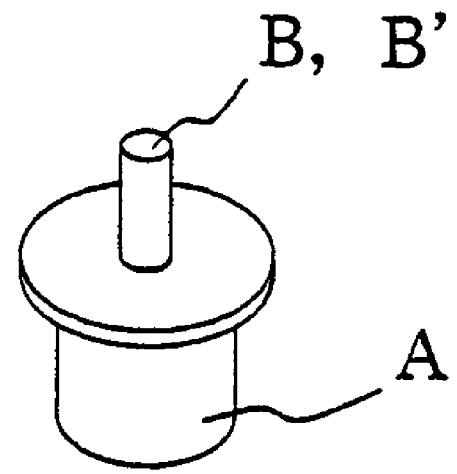
FIG. 5 is a perspective view showing an example of the conventional anode.

FIG. 4 shows an embodiment of the anode 6 described earlier. A sheet of material having a corrosion resistance to the electrolyte, good workability and electrical conductivity, and having no electrochemical action on the anode, such as nickel, is formed, by stamping or etching, into a piece comprising an annular electrode segment 20 and the lead 7, as shown in FIG. 4(*a*). Then, a layer of lead 21 of amount appropriate for the sensor life is coated on the electrode segment as shown in FIG. 4(*b*).

This layer of lead 21 is formed by using a plating bath comprising, for example, 200 parts $PbCO_3$, 100 parts $HBF_4$, 15 parts $H_3BO_3$, and 0.2–0.5 part gelatin, with the portion to be used as the lead 7 not immersed in the bath or kept out of contact therewith by using a resist medium. The anode 6 having the lead 7 not coated with lead is formed by controlling the amount of lead coated on the electrode segment 20 by passing an electric current for a time corresponding to the amount of electric charge appropriate for the sensor life.

The electrolyte is either preliminarily impregnated into the sheet 5 or poured into a hollow space 11 through an opening in the electrode-holding frame 1 before the circuit board 1 is placed in position.

What is claimed is:

1. A galvanic-cell gas sensor comprising:

a casing containing a diaphragm, said diaphragm being permeated by a gas to be detected but having a water-repelling property;

a cathode provide on a back side of the diaphragm;

an anode having a layer of Pb on a conductive material having a corrosion resistance to an electrolyte so as to leave a portion thereof uncoated to serve as an anode lead; and a sheet preliminarily impregnated with the electrolyte and disposed between said cathode and anode, wherein said diaphragm is positioned so as to be exposed to an external atmosphere, and wherein said preliminarily impregnated sheet is arranged without communicating with a liquid electrolyte reservoir.

2. A galvanic-cell gas sensor according to claim 1, in which said cathode has a convexly shaped top surface and is fit in the upper part of a through hole at the center of a closed-end cylindrical electrode-holding frame and said diaphragm is mounted on top of said electrode-holding frame and curved along said convexly shaped top surface of the cathode under the pressure of a cap of elastic material having a center through hole.

3. A galvanic-cell gas sensor according to claim 2, in which an annular groove is provided outside the through hole in the electrode-holding frame and said diaphragm is fastened to said electrode-holding frame with an adhesive outside said groove.

4. A galvanic-cell gas sensor according to claim 2, wherein said anode is contained in said electrode-holding frame, said anode lead is withdrawn from said electrode-holding fame and pulled outside through a small hole in said cap.

5. A galvanic-cell gas sensor according to claim 4, wherein the anode lead is held in contact with a conductive case constituting a portion of said casing, and an end of a cathode lead of said cathode is connected to a circuit board and brought into contact with a conductive bottom cap constituting another portion of said casing through a conductive pattern on said circuit board, wherein said casing and said conductive bottom cap are insulated from each other and fastened by caulking.

6. A galvanic-cell gas sensor according to claim 5, wherein said conductive pattern is connected to said anode along a periphery of a surface of said circuit board facing said bottom cap and a resistance is connected to said anode and cathode.

7. The galvanic-cell sensor of claim 1, wherein an amount of Pb on the conductive material is selected based on a desired sensor life.

8. The galvanic-cell gas sensor of claim 1, wherein the preliminary impregnated sheet is impregnated with the electrolyte before the galvanic-cell gas sensor is assembled.

9. A galvanic-cell gas sensor, comprising:

a gas-permeable diaphragm, said diaphragm being positioned so as to expose one side of the diaphragm to an external atmosphere;

a cathode provide on an opposite side of the diaphragm;

an anode; and a sheet impregnated with an electrolyte and disposed between said cathode and anode, wherein said anode includes a conductive material having a first portion with a layer of Pb and a second portion which is free of Pb, wherein an amount of Pb establishes a sensor life.

10. The galvanic-cell gas sensor of claim 9, wherein said layer of Pb is a coated layer of Pb.

11. The galvanic-cell gas sensor of claim 9, wherein said sheet impregnated with an electrolyte does not communicate with a liquid electrolyte reservoir.

* * * * *

UNITED STATES PATENT AND TRADEMARK OFFICE
CERTIFICATE OF CORRECTION

PATENT NO. : 6,436,258 B1  
DATED : August 20, 2002  
INVENTOR(S) : Shoichi Uchikoshi It is certified that error appears in the above-identified patent and that said Letters Patent is hereby corrected as shown below:

<u>Title page,</u>  
Item [73], assignee's name should read: -- Riken Keiki Co., Ltd., Tokyo (JP) --

Signed and Sealed this

Twenty-eighth Day of January, 2003

JAMES E. ROGAN  
*Director of the United States Patent and Trademark Office*